US008680061B2

(12) United States Patent
Archakov et al.

(10) Patent No.: US 8,680,061 B2
(45) Date of Patent: Mar. 25, 2014

(54) MEDICINAL FORMS OF PHOSPHOLIPID PREPARATIONS AND METHODS FOR THEIR PREPARATION

(75) Inventors: Alexandr Ivanovich Archakov, Moscow (RU); Mariya Kirillovna Guseva, Moskovskaya obl. (RU); Vasiliy Fedorovich Uchaikin, Moscow (RU); Elena Georgievna Tikhonova, Moscow (RU); Olga Mikhailovna Ipatova, Moscow (RU)

(73) Assignee: Alexandr Ivanovich Archakov, Moscow (RU)

( * ) Notice: Subject to any disclaimer, the term of this patent is extended or adjusted under 35 U.S.C. 154(b) by 738 days.

(21) Appl. No.: 12/063,581

(22) PCT Filed: Aug. 11, 2006

(86) PCT No.: PCT/IB2006/002195
§ 371 (c)(1),
(2), (4) Date: Jun. 9, 2008

(87) PCT Pub. No.: WO2007/020505
PCT Pub. Date: Feb. 22, 2007

(65) Prior Publication Data
US 2010/0179100 A1 Jul. 15, 2010

(30) Foreign Application Priority Data
Aug. 12, 2005 (RU) ................................ 2005125634

(51) Int. Cl.
*A61K 9/127* (2006.01)
*A61K 9/19* (2006.01)
*A61K 47/12* (2006.01)
*A61K 31/704* (2006.01)

(52) U.S. Cl.
USPC ........................................................ 514/33

(58) Field of Classification Search
USPC ........................................................ 514/33
See application file for complete search history.

(56) References Cited

FOREIGN PATENT DOCUMENTS

| CN | 1569005 A | 1/2005 |
| CN | 1594332 A | 3/2005 |
| CN | 1686151 A | 10/2005 |
| CN | 1709343 A | 12/2005 |
| DE | 4002166 A1 | 8/1991 |
| EP | 0 556 394 A1 | 8/1993 |
| RU | 2133122 * | 7/1999 |
| RU | 2133122 C1 | 7/1999 |
| RU | 2196585 C2 | 1/2003 |

OTHER PUBLICATIONS

Seki et al, Int. J. Pharm. 2004, 273 (1-2), 75-83; English abstract.*
Hamilton et al, J. Lipid Res. 1980, 21, 981-92.*
"Database Accession No. PREV200200545266", Mar. 2002, Biosciences Information Service, BIOSIS, Philadelphia, PA, US.
Tsuji, Hideki, et al., "Targeting of liposomes surface-modified with glycyrrhizin to the liver I. Preparation and biological disposition", "Chem. Pharm. Bull.", 1991, pp. 1004-1008, vol. 39, No. 4, Publisher: Pharmaceutical Society of Japan.
"Database Accession No. 138:390895", May 13, 2003, Publisher: Chemical Abstracts Service, CAPLUS, Published in: Columbus, Ohio, US.
"Database Accession No. 144:164212", Feb. 23, 2006, Publisher: Chemical Abstracts Service, CAPLUS, Published in: Columbus, Ohio, US.
"Database Accession No. 144:57406", Nov. 21, 2005, Publisher: Chemical Abstracts Service, CAPLUS, Published in: Columbus, Ohio, US.
"Database Accession No. 145:130815", Jul. 11, 2006, Publisher: Chemical Abstracts Service, CAPLUS, Published in: Columbus, Ohio, US.
"Database Accession No. 145:477838", Nov. 30, 2006, Publisher: Chemical Abstracts Service, CAPLUS, Published in: Columbus, Ohio, US.
Guseva, Mariya et al.,Unpublished Co-Pending U.S. Appl. No. 12/063,585, "Medicinal Forms of Phospholipid Preparations and Methods for Their Preparation".
Drummond, D., et al., "Optimizing Liposomes for Delivery of Chemotherapeutic Agents to Solid Tumors", "Pharmacological Reviews", 1999, pp. 691-743, vol. 51, No. 4.
Moghimi, S., et al., "Long-Circulating and Target-Specific Nanoparticles: Theory to Practice", "Pharmacological Reviews", 2001, pp. 283-318, vol. 53, No. 2.
Seki, J., et al., "A nanometer lipid emulsion, lipid nano-sphere (LNS), as a parenteral drug carrier for passive drug targeting.", "Int. J. Pharm.", Apr. 1, 2004, pp. 75-83 (Abstract Only), vol. 273, No. 1-2.
Note: For the non-patent literature citiations that no month of publication is indicated, the year of publication is more than 1 year prior to the effective filing date of the present application.
Fenske, D., et al., "Liposomal Nanomedicines: An Emerging Field", "Toxicologic Pathology", Jan. 2008, pp. 21-29, vol. 36, No. 1.
Fricker, G., et al, "Phospholipids and Lipid-Based Formulations in Oral Drug Delivery", "Pharm Res", Apr. 22, 2010, pp. 1469-1486, vol. 27.
Luisi, P., "The Emergence of Life From Chemcial Origins to Synthetic Biology", Jul. 2006, pp. 199-205, Publisher: Cambridge University Press.

* cited by examiner

*Primary Examiner* — Ganapathy Krishnan
(74) *Attorney, Agent, or Firm* — Hultquist, PLLC; Steven J. Hultquist

(57) ABSTRACT

A method for producing a pharmaceutical composition comprising a combination of phospholipid and glycyrrhizic acid or a pharmaceutically acceptable salt thereof, which composition is hydratable to produce an injectable medicinal form, said method comprising subjecting a mixture of phospholipid and an aqueous solution of glycyrrhizic acid or a pharmaceutically acceptable salt thereof and a carbohydrate to homogenization, for example at 800-1200 bar pressure at a temperature of less than 90° C., and subjecting the product of the homogenization to a sublimation drying step to produce said composition. Compositions obtainable using this method, and hydrated forms of these ready for administration by injection form further aspects of the invention.

13 Claims, No Drawings

MEDICINAL FORMS OF PHOSPHOLIPID PREPARATIONS AND METHODS FOR THEIR PREPARATION

CROSS-REFERENCE TO RELATED APPLICATIONS

This application is a U.S. national phase patent application filed under the provisions of 35 USC §371 based on International Application No. PCT/IB06/02195 filed Aug. 11, 2006, which in turn claims priority of Russian Federation Patent Application No. 2005125634 filed Aug. 12, 2005. The disclosures of such international application and Russian Federation priority application are hereby incorporated herein by reference in their respective entireties, for all purposes.

The invention relates to the area of pharmaceutics and concerns the production technology of injectable medicinal forms of phospholipid preparation, in particular those sold as "Phosphogliv" for treatment and prevention of acute and chronic liver diseases, lipid exchange disorder and restoration of liver function after intoxication. The above-mentioned preparation contains vegetative phospholipids, glycyrrhizic acid or its salts and auxiliary substances.

It is known that liver pathological processes of various diseases are accompanied by the structural and functional damage of membrane hepatocyte systems. Damage to membranes is caused by lipid stratum disorder due to the involvement of lipids in the processes of peroxidation and endogenous phospholipase activity. Any change in the physicochemical properties of lipids can result in structural damage to lipid biomembrane matrix and loss of their barrier function that is accompanied by inactivation of membrane enzyme systems.

It has been shown in numerous research studies (including some conducted by the Institute of Biomedical Chemistry of the Russian Academy of Medical Sciences) that the most effective phospholipids for use in the restoration of the damaged hepatocyte membranes are phospholipids derived from vegetative material. Such vegetative phospholipids incorporate essential fatty acids (linoleic and linolenic acid), which make them more liquid than usual membrane phosphatidylcholine. This seems to allow them to play the role of "membrane glue", capable to repair defects of the damaged cellular membranes more effectively. The mechanism of action of vegetative phospholipids appears to be due to the inclusion of polyunsaturated phosphatidylcholine into membranes and it is capable to restore the structure and function of the damaged cells.

Therefore the development of effective medicinal forms which incorporate phospholipids remains important.

There are a number of preparations which include phospholipids, which are produced in capsules, dragee or pills, and also injectable forms.

"Essentiale" is one of such preparations which has been applied in practical public health services more than 40 years to restore liver functions. A more recent preparation is sold as "Essentiale H" (Natterman Co. Germany) and contains a mixture of phospholipids, unsaturated fatty acids and vitamins.

A salt of deoxycholic acid is used as a detergent in the production technology of injectable forms of "Essentiale" for dissolution of fatty phospholipid substance. However, this is disadvantageous as it has a degree of cytotoxicity and so may negatively influence cells.

There is also another known phospholipid preparation, "Phosphogliv", which is used for the treatment and prevention of liver disease, it contains vegetative phospholipids with a high phosphatidylcholine content (75-98%) as well as glycyrrhizic acid, salts and additional ingredients. Glycyrrhizic acid and its salt, can act as an emulsifier, but also possesses hepatoprotector, antiinflammatory, anti-allergic and anti-viral properties, besides having a mild detergent effect. Injectable formulations of this preparation are known. They take the form of dried liposomal preparations, which are hydrated for use.

The applicants have found however that the injectable forms of the compositions are difficult to obtain using conventional methods and may suffer in that the liposomal particles may be non-uniform and rather large in size, with a tendency to aggregate on storage. After storage for 4-6 months for example lyophilized powder preparation produces turbid solutions, because the liposomal/micellar structure is not preserved and the particles become enlarged. Therefore the shelf-life of these preparations is usually limited to 3 months only.

Furthermore, an increase in the content of oxidized phospholipids, in particular, lysophosphatidylcholine is also frequently observed. According to regulatory requirements, the contents of lysophosphatidylcholine, in ready-to-use preparation should not exceed 3% and where higher levels occur, the product cannot be used in medical practice.

The applicants have found a preparation route that reduces or eliminates some of these problems. According to the present invention there is provided a method for producing a pharmaceutical composition.

As used herein, the term "nanoparticles" means that at least some, and suitably a substantial proportion of the particles within the emulsions are less than 100 nm in size (for example diameter).

In order to achieve this, homogenisers which operate using pressure or ultrasound may be employed. In particular the homogenizer used is a device which subjects the mixture to cycling under pressure.

Homogenisation pressures in excess of 600 bars may be employed. However, in a particularly preferred embodiment, the mixture is subject to homogenization at relatively high pressures, for example at pressures from 800-1200 bar The applicants have found that compositions with improved properties, may be achieved using this method particularly.

Suitably the homogenization is effected at a temperature below 90° and suitably in range of from 20-50° C., for example from room temperature to 46° C. and conveniently at room temperature.

The precise number of homogenization cycles can be varied depending upon the nature of the homogenizer etc., but preferably the number of cycles is sufficient to produce, after drying, a preparation comprising liposomal particles of a size of from 20-100 nm, for instance up to 60 nm, more suitably up to 50 nm, yet more suitably up to 40 nm and preferably up to 30 nm in diameter. Typically, the mixture is subjected to from 5 to 22 homogenization cycles.

Suitably the product of the homogenization is subjected to filtration prior to sublimation drying. This may be carried out for example using a membrane under an inert atmosphere, for example of nitrogen. Preferably the sublimation drying is conducted slowly under relatively mild conditions. The amount of time will depend upon factors such as the hatch size etc., but typically will be over a period of days.

Suitably a sterilizing filtration step is effected in a sterile room, for example using pressure filtration, for example under pressure of about 3 atmospheres.

The ratio of phospholipid to glycyrrhizic acid or pharmaceutically acceptable salt thereof in the pharmaceutical composition is suitably not greater than 4:1 and is preferably in the range of from 0.5:1 to 4:1.

The pharmaceutical composition obtained suitably comprises from 2-80% w/w total phospholipid and glycyrrhizic acid or pharmaceutically acceptable salt thereof.

In a particular embodiment the phospholipid used is obtained from a vegetative source such as soybean extract, which suitably comprises from 75-98% w/w of phosphatidylcholine.

The carbohydrate used in the method is suitably selected from maltose, lactose or isomaltose. The amount of carbohydrate included will be variable and will depend upon conditions used, but it may comprise the balance of the pharmaceutical composition, and therefore may be present in the range of from for example, 20-98% w/w.

Suitably the pH of the solution used in the method is in the range of from 6.0 to 7.5, preferably from 6.5 to 7.5. In a particular embodiment, an aqueous solution of glycyrrhizic acid or pharmaceutically acceptable salt thereof is prepared and phospholid dispersed into it, for example so as to form an emulsion. A separately prepared aqueous solution of carbohydrate is then added before the resultant mixture is subjected to homogenization.

Pharmaceutical compositions obtainable by a method described above as well as injectable pharmaceutical composition obtainable by hydration of such compositions form a further aspect of the invention.

Compositions obtained as described above have been found to be homogenous with a good size range of nanoparticles. Using the method described above, finely dispersed, homogeneous and stable liposomal particles (20-100 nm) are obtained, 95% of the particles are in the 20-35 nm size range, which gives rise to a stable solution, most appropriate for intravenous introduction. Uniformity of particles provides for high transparency and stability of solution. Furthermore, compositions obtained in this way have been found to be particularly stable, and it has been found that the structure can be restored at dissolution in water even after a three-year storage period.

They can be used for the treatment and prevention of liver diseases, lipid exchange disorder and/or restoration of liver function after intoxication, and are administered by injection, for example intravenously.

The following examples illustrate the invention:

EXAMPLE 1

Solution A:

6.9 g of dynatrium salt of GA was dissolved in water for injections and the volume made up to 90 ml. NaOH (2.25 ml, 1N) was added (sufficient to produce a pH in the final 300 ml volume of from 6.7-7.5). Crushed phospholipid (16.5 g) with a phosphatidylcholine content of 80% was added. Dispersion was carried out using a highly effective propeller mixer in a current of inert gas (nitrogen).

Solution B:

Maltose (59.4 g) was dissolved in water for injection and carefully mixed until the solution became transparent and the final volume was made up to 150 ml. It would be possible to add additional water, provided that the volume of solution A+the volume of solution B<300 ml.

Solutions A and B were then mixed together and the total volume made up to 300 ml by water for injection.

Homogenization of Solution

The solution was passed through a homogenizer (model Mini-Lab 7.30 VH, Rannie, Denmark) for 60 minutes under a pressure of 800 bar. Cooling was carried out through a backflow condenser. Homogeneous liposomes with diameter 40-60 nm were obtained at this stage. Transparency of the sample (660 nm) after homogenization was not less than Prefiltration The homogenized solution was filtered under nitrogen at a pressure of 2 atmospheres through a membrane ("Vladipor", 3-4 micron). The transparency of the solution (660 nm) was not less than 60%.

Sterilizing Filtration

Sterilizing filtration was carried out in a sterile room in laminar air flow (Laminarbox LB-G, Russia) with the help of a pressure filtering device (PNF-90, Joint-Stock Company "Membranes", Russia) through filter ("Vladipor"), 0.2 μm in diameter under pressure of 3 atmospheres. The transparency of the solution was approximately 65%.

Sterile Pouring in Bottles

The solution was poured into 10 ml dark bottles by closer in a laminar stream of sterile air and was frozen at −25° C.

Sublimation Drying of Aqueous Solution

The frozen samples were exposed to sublimation drying (LSL SECFROID, LYOLAB F, Germany) for a period of 48 hours. A homogeneous liposomal composition of dense consistency was obtained. Bottles were sealed with aluminium capsules.

Samples were stored for three years at room temperature, after which they "were hydxated with water, and the structure was successfully restored.

Further examples are illustrated in the following table.

Table of nanoparticle (micelles) size (diameter) in a "Phophogliv" Lyophilizate for preparation of solution for intravenous injection

| No. | Contents PC*% in PL** | T % (660 nm) (transparency) | Average Size of nanoparticles (nm) | Number of homogenization cycles, mode, temperature, etc. | Total contents PL** and GA***; % | Ratio PL and GA |
|---|---|---|---|---|---|---|
| 2 | 75 | 70% | 1. 22 nm (96%) and 68 nm (4%) 2. 22 nm (94%) and 77 nm (6%) 3. 26 nm (95%) and 73 nm (7%) 4. 22 nm (95%) and 75 nm (5%) 5. 20 nm (90%) and 54 nm (10%) | 9 cycles of homogenization at 1000 bar pressure Temperature 45° C. pH 6.85 | 2% | 4:1 |
| 3 | 75 | 72% | 21 ± 1.9 nm (44% ± 10%) and 51 ± 7.6 nm (47.1% ± 14%) | 22 cycles of homogenisation at 1200 bar pressure | 2% | 3:1 |

Table of nanoparticle (micelles) size (diameter) in a "Phophogliv" Lyophilizate for preparation of solution for intravenous injection

| No. | Contents PC*% in PL** | T % (660 nm) (transparency) | Average Size of nanoparticles (nm) | Number of homogenization cycles, mode, temperature, etc. | Total contents PL** and GA***; % | Ratio PL and GA |
|---|---|---|---|---|---|---|
| 4 | 80 | | 27.2 ± 7.6 nm (66.2% ± 13.4%); 70 ± 12.3 nm (34% ± 10%) 28.5 ± 7.4 nm (60% ± 18%); 71.1 ± 9.8 nm (43% ± 12%) 25.4 ± 4.3 nm (80% ± 10%); 70.1 ± 13.8 (20% ± 10%) | Temperature 40° C. (500 ml sample) 10 cycles of homogenization at 1000 bar pressure Temperature 45° C. | 5% | 2.5:1 |
| 5 | 98 | 69% | 20 ± 1 and 44 ± 5; 20 ± 4 and 39 ± 2; 21 ± 3 and 53 ± 10; 24 ± 6 and 54 ± 8; 25 ± 5 and 55 ± 10 | 14 cycles of homogenization at 800 bar pressure, Temperature 43° C. pH 6.2 | 30% | 2.0:1 |
| 6 | 98 | 64%; 71% after subl. | 22 ± 2.8 nm (47%) 53 ± 8 nm (43%) 110 ± 8.3 nm (10%) (after lyophilisation) | 1500 ml solution was processed as 3 samples of 500 ml, each passed through 7 cycles of homogenization pH 6.8 | 80% | 1:1 |
| 7 | 80 | 1) 61.5% 2) 69% 3) 66% 71% after subl. | Before drying 21 ± 7 nm (42% ± 4%); 60 ± 3.3 nm (57.5% ± 5%) after drying 24 ± 5 nm (65% ± 10.5%); 71 ± 11 nm (35% ± 9%) | 1500 ml solution was processed as 3 samples of 500 ml, 1) 15 cycles homogenisation at 800 bar, 2) 6 cycles homogenisation at 1100 bar 3) 8 cycles of homogenisation at 1000 bar, transparency before filtration and of combination of 3 parts before drying. Temperature 46° C. pH 6.69 | 80% | 2.5:1 |
| 8 | 78 | 76% | 75.88 nm (1.62% by mass) 23.02 nm (98.38% by mass) | Homogenization within 5 Cycles at 1000 bar, Temp (start) 40° C., Temp (average) 45° C. | 50% | 0.5:1 |
| 9 | 85 | 78% | 58.80 nm (1.01% by mass) 19.02 nm (98.83% by mass) | Homogenization within 6 Cycles at 1000 bar, Temp (start) 40° C., Temp (average) 45° C. | 80% | 1.5:1 |
| 10 | Series 020902 | From 71.4% to 74.6% | 8550.57 nm (9.64% by mass) 133.06 nm (0.34% by mass) 34.91 nm (90.03% by mass) The same series, but another bottle 6657.81 nm (6.65% by mass) 297.46 nm (0.07% by mass) 41.09 nm (93.28% by mass) The 3rd bottle series 02.09.02 9063.63 nm (6.54% by mass) 139.63 nm (0.25% by mass) 35.20 nm (93.22% by mass) | Homogenization within 10 Cycles at 1000 bar, t (start) 40° C., T (average) 45% | 10% | 2.5:1 |
| 11 | 80 | 67% | 7876.79 nm (5.26% by mass) 87.70 nm (0.39% by mass) 21.79 nm (94.35% by mass) | Homogenization within 8 Cycles at 1000 bar, Temp (start) 40° C., Temp (average) 45° C. | 20% | |

PC*—phosphatidylcholine
PL**—phospholipid
GA***—glycyrrhizic acid or its salt

The described method results in the production of a stable, highly effective preparation with a good size of nanoparticles which can be used in clinical practice for complex treatment of the various diseases involving liver function disorders.

Clinical trials have shown that the preparation ("Phosphogliv") which may be obtained as described above, as a lyophilizate for intravenous introduction solution, had high efficiency for treatment of liver diseases of various etiology. The intravenous form of the preparation is tolerated by patients and does not give rise to significant side effects and results in appreciable improvement of clinical tests and the general condition of patients. The preparation influences the replicative activity of hepatitis B and C, and also the immune and interferon status indicating that it may be useful for the treatment of chronic viral hepatitis and other diseases associated with liver damage.

The invention claimed is:
1. A method for producing a pharmaceutical composition comprising a combination of phospholipid and glycyrrhizic acid or a pharmaceutically acceptable salt thereof, which composition is hydratable to produce an injectable medicinal form, said method comprising subjecting a mixture of phospholipid and an aqueous solution of glycyrrhizic acid or a pharmaceutically acceptable salt thereof and a carbohydrate to homogenization under a pressure of from 800-1200 bar and at a temperature of between 20 and 50° C. where the mixture is subjected to from 5 to 22 homogenization cycles to form an emulsion comprising nanoparticles, and subjecting a product of the homogenization to a sublimation drying step to produce said composition having finely dispersed, homogenous and stable particles of a size of 20-100 nm, with 95% of said nanoparticles being of a size of 20-35 nm wherein the phospholipid used is from a vegetative extract having from 75-98% of phosphatidylcholine and the ratio of phospholipid to glycyrrhizic acid or pharmaceutically acceptable salt is not greater than 4:1.

2. A method according to claim 1 which is conducted in a homogenizer which subjects the mixture to pressure.

3. A method according to claim 2 wherein the homogenization is conducted at room temperature.

4. A method according to claim 1 wherein the product of the homogenization is subjected to filtration prior to sublimation drying.

5. A method according to claim 4 wherein the filtration comprises a preliminary filtration step, followed by a sterilizing filtration step.

6. A method according to claim 1 wherein the total content of phospholipid and glycyrrhizic acid or pharmaceutically acceptable salt thereof in the pharmaceutical composition is from 2-80% w/w of the pharmaceutical composition.

7. A method according to claim 1 wherein the carbohydrate comprises maltose, lactose or isomaltose.

8. A method according to claim 1 wherein the pH of the solution is in the range of from 6.5 to 7.5.

9. A pharmaceutical composition having finely dispersed homogenous and stable particles of a size of 20-100 nm, with 95% of said nanoparticles being of a size of 20-35 nm obtainable by a method according to claim 1.

10. An injectable pharmaceutical composition obtainable by hydration of a composition according to claim 9, the composition having finely dispersed homogenous and stable particles of a size of 20-100 nm, with 95% of said nanoparticles being of a size of 20-35 nm.

11. A method for producing a pharmaceutical composition comprising a combination of phospholipid and glycyrrhizic acid or a pharmaceutically acceptable salt thereof, which composition is hydratable to produce an injectable medicinal form, said method comprising subjecting a mixture of phospholipid and an aqueous solution of glycyrrhizic acid or a pharmaceutically acceptable salt thereof and a carbohydrate to homogenization under a pressure of from 800-1200 bar and at a temperature of between 20 and 50° C. where the mixture is subjected to from 5 to 22 homogenization cycles to form an emulsion comprising nanoparticles, and subjecting a product of the homogenization to a sublimation drying step to produce said composition having finely dispersed, homogenous and stable particles in a particle size range conferring stable solution character of said particles in water, wherein the particle size range is up to 40 nm and wherein the phospholipid used is from a vegetative extract having from 75-98% of phosphatidylcholine and the ratio of phospholipid to glycyrrhizic acid or pharmaceutically acceptable salt is not greater than 4:1.

12. A pharmaceutical composition obtainable by the method of claim 11.

13. A method for producing a pharmaceutical composition comprising a combination of phospholipid and glycyrrhizic acid or a pharmaceutically acceptable salt thereof, which composition is hydratable to produce an injectable medicinal form, said method comprising subjecting a mixture of phospholipid and an aqueous solution of glycyrrhizic acid or a pharmaceutically acceptable salt thereof and a carbohydrate to homogenization under a pressure of from 800-1200 bar and at a temperature of between 20 and 50° C. where the mixture is subjected to from 5 to 22 homogenization cycles to form an emulsion comprising nanoparticles, and subjecting a product of the homogenization to a sublimation drying step to produce said composition having finely dispersed, homogenous and stable particles of a size of 20-100 nm, with 95% of said nanoparticles being of a size of 20-35 nm, wherein the ratio of phospholipid to glycyrrhizic acid or a pharmaceutically acceptable salt thereof is not greater than 4:1 and wherein the total content of phospholipid and glycyrrhizic acid or pharmaceutically acceptable salt thereof in the pharmaceutical composition is from 2-80% w/w of the pharmaceutical composition and wherein the phospholipid used is from a vegetative extract having from 75-98% of phosphatidylcholine.

* * * * *

UNITED STATES PATENT AND TRADEMARK OFFICE
CERTIFICATE OF CORRECTION

| | | |
|---|---|---|
| PATENT NO. | : 8,680,061 B2 | Page 1 of 1 |
| APPLICATION NO. | : 12/063581 | |
| DATED | : March 25, 2014 | |
| INVENTOR(S) | : Alexandr Ivanovich Archakov et al. | |

It is certified that error appears in the above-identified patent and that said Letters Patent is hereby corrected as shown below:

On the title page of the printed patent, Item (30) under Foreign Application Priority Data:
"2005125634"
should be
--2005125633--.

In the Specification

Column 1, line 12: "2005125634" should be --2005125633--.

Column 4, line 25:
"...after homogenization was not less than"
should be
--"...after homogenization was not less than 60%.--.

Signed and Sealed this
First Day of July, 2014

Michelle K. Lee
*Deputy Director of the United States Patent and Trademark Office*